United States Patent [19]
Kumagai et al.

[11] Patent Number: 5,339,093
[45] Date of Patent: Aug. 16, 1994

[54] LIQUID CRYSTAL PANEL INSPECTION METHOD

[75] Inventors: Eryohei Kumagai; Kaoru Hiiro; Harumi Shimizu; Tooru Takahashi, all of Tokyo, Japan

[73] Assignee: Ezel, Inc., Tokyo, Japan

[21] Appl. No.: 801,356

[22] Filed: Dec. 2, 1991

[30] Foreign Application Priority Data

Dec. 4, 1990 [JP] Japan .................... 2-404006

[51] Int. Cl.$^5$ ............................................. G09G 3/36
[52] U.S. Cl. ................................... 345/149; 345/87; 345/904; 324/770
[58] Field of Search ............... 340/784, 715, 765, 716; 382/8; 73/603, 800; 324/527, 158 R, 158 T, 73.1; 345/87, 89, 147, 148, 904

[56] References Cited

U.S. PATENT DOCUMENTS

| | | | |
|---|---|---|---|
| 4,513,441 | 4/1985 | Henshaw | 382/43 |
| 5,014,326 | 5/1991 | Turner et al. | 382/8 |
| 5,017,755 | 5/1991 | Yahagi et al. | 219/121.68 |
| 5,081,687 | 1/1992 | Henley et al. | 382/8 |
| 5,115,229 | 5/1992 | Shulit | 340/716 |
| 5,162,785 | 11/1992 | Fagard | 340/765 |

FOREIGN PATENT DOCUMENTS

348703  1/1990  European Pat. Off. .

OTHER PUBLICATIONS

Mandeville, J., "Novel Method for Analysis of Printed Circuit Images", *IBM Journal of Research and Development*, vol. 29, No. 1, Jan. 1985, Armonk, N.Y., pp. 73–86.

Darwish, et al., "A Rule Based Approach for Visual Pattern Inspection", *IEEE Transactions on Pattern Analysis and Machine Intelligence*, vol. 10, (1988) Jan., No. 1, New York, N.Y., pp. 56–68.

Chin, et al., "Automated Visual Inspection: A Survey", *IEEE Transaction on Pattern Analysis and Machine Intelligence*, vol. PAMI-4 (1982) No. 6, New York, N.Y., pp. 557–573.

*Primary Examiner*—Alvin E. Oberley
*Assistant Examiner*—Steve Saras
*Attorney, Agent, or Firm*—Cushman, Darby & Cushman

[57] ABSTRACT

The present invention makes it possible for unskilled to inspect the total surface of a liquid crystal panel accurately in short time. It is defined that a liquid crystal panel can be divided into a single part which is a constituent, isolable, and an inspectable area, and that the single part to be "unit area of image" which is defined as a pattern to be inspected. Before the inspection, a unit area of an image without defect is selected from a liquid crystal panel to be inspected. The upper limit reference pattern and the lower limit reference pattern are generated by giving the maximal brightness in a convolution and adding the predetermined brightness and by giving the minimal brightness in the convolution and subtracting the predetermined brightness, respectively, to each pixel of the convolution. Comparing a brightness of each pixel of the upper limit and the lower limit reference pattern with a brightness of a pixel of a pattern to be inspected corresponding to it, the liquid crystal panel to be inspected is judged to be up to standard when more than a predetermined number of pixels are within the range between the upper limit and the lower limit brightness of the reference pattern.

7 Claims, 3 Drawing Sheets

LIQUID CRYSTAL PANEL INSPECTION METHOD

FIELD OF THE INVENTION

The present invention relates to an inspection method for a liquid crystal panel used for a display device of a computer and for similar applications.

BACKGROUND OF THE INVENTION

When liquid crystal panels are manufactured, several percent of the yield are often defective. Conventionally, the defective products are identified by visual inspection. First, observing the luminosity of the surface of a panel when energized, the defective parts are roughly determined. Next, observing each part of a defective liquid crystal panel in detail, it is determined where the defective parts are and how the parts are defective.

SUMMARY OF THE INVENTION

Such visual inspection is, however, very difficult. It takes several hours to inspect one liquid crystal panel even for one skilled in the art of inspection.

An inspection method for automatic inspection of intergrated circuit may be applicable to inspection of liquid crystal panels. This method is a pattern matching method, in that an IC image is compared with a blueprint or reference pattern. Since the parts on the liquid crystal has a thickness and is substantially three-dimensional, the edges of the parts appear as shadowy lines, differently from the flat surface of an intergrated circuit. The input apparatus for the image of a liquid crystal is adjusted not to take the shadowy lines into account; however, a part of the lines may be inputted due to optical aberration and light conditions. In such an image, it is impossible to determine defective parts reliably by comparing the parts with a template.

The present invention has been developed to provide a liquid crystal panel inspection method, by which it is possible for the unskilled individual to inspect a liquid crystal in a short time.

A liquid crystal panel comprises an array of parts with a common shape. Each of these parts may be considered to be a "unit area" which is inspected through comparison with a reference image. The present inspection method of a liquid crystal panel for judging if it is defective or not by comparing a pattern to be inspected with a reference pattern recorded beforehand is characterized in the following steps: i) a unit of an image without defects is selected from a liquid crystal panel to be inspected before an inspection; ii) the upper limit reference pattern and the lower limit reference pattern are generated by giving the maximal brightness in a convolution and adding the predetermined brightness and by giving the minimal brightness in the convolution and subtracting the predetermined brightness, respectively, to each pixel of the convolution; iii) a brightness of each pixel of the upper limit and the lower limit reference pattern are compared with a brightness of a pixel of a pattern to be inspected corresponding to it; iv) the liquid crystal panel to be inspected is judged to be up to the standard, that is, recognized to be defectless when more then a predetermined number of pixels are within the range between the upper limit and the lower limit brightness of the reference pattern.

PREFERRED EMBODIMENT OF THE PRESENT INVENTION

Hereinafter, the present invention is described referring to the attached drawings.

Figure 3:
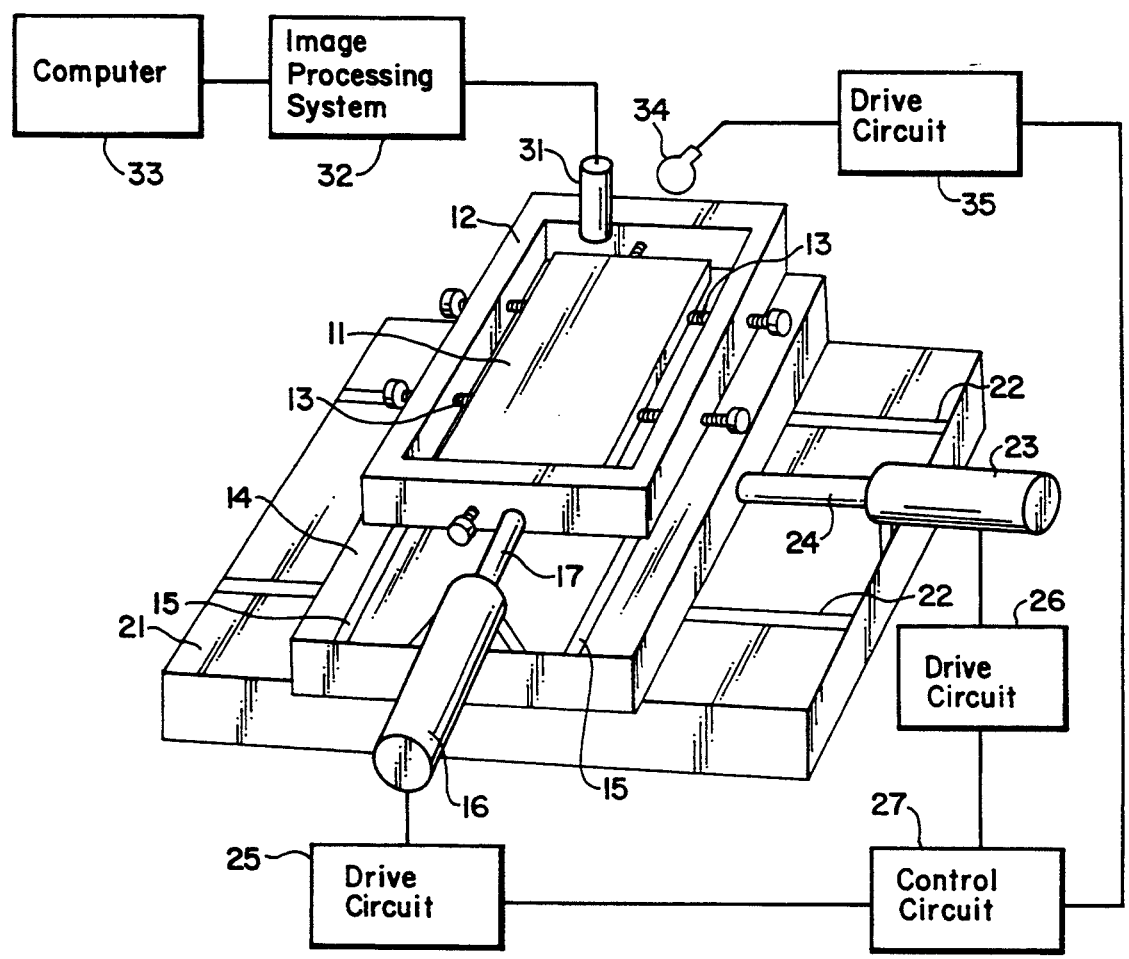
FIG. 3 shows a perspective view of an apparatus used for the inspection method of this invention.

FIG. 3 shows an apparatus used for the present invention. A liquid crystal panel 11 is located inside of a support frame 12 so as to fixed on the frame 12 with bolt 13. Support frame 12 movable mounted on a pair of rails 15 on a is movably plate 14. A cylindrical device 16 is be fixedly mounted on the end of is movably plate 14, whose piston rod 17 is connected to the support frame 12. Movable plate 14 is movably mounted on a pair of rails 22 on fixed plate 21. Similar to the movable plate 14, the fixed plate 21 is provided with a cylindrical device 23 at one end whose piston rod 24 is connected to the movable plate 14.

Support frame 12 is moved in parallel to movable frame 14 by controlling cylinder device 16, and movable plate 14 is moved in parallel to fixed plate 21 by controlling cylinder device 23. Cylinder devices 16 and 23 are driven by drive circuits 25 and 26, respectively, so as to move the piston rods 17 and 24 forward or backward. Drive circuits 25 and 26 are controlled by a control circuit 27.

A microscope 31 is supported by a fixed frame (not shown) above the liquid crystal panel 11. Each pattern is inputted through the microscope 31, as described later. The image of this pattern is inputted to image processing system 32 and various processings are performed therein. Image processing system 32 is controlled by computer 33.

Light source 34, such as a stroboscope, is provided for lighting the support frame 12 from above. It is fixed to support frame 12 and moves with it. Light source 34 is driven by a drive circuit 35 which is controlled by control circuit 27.

Figure 1:
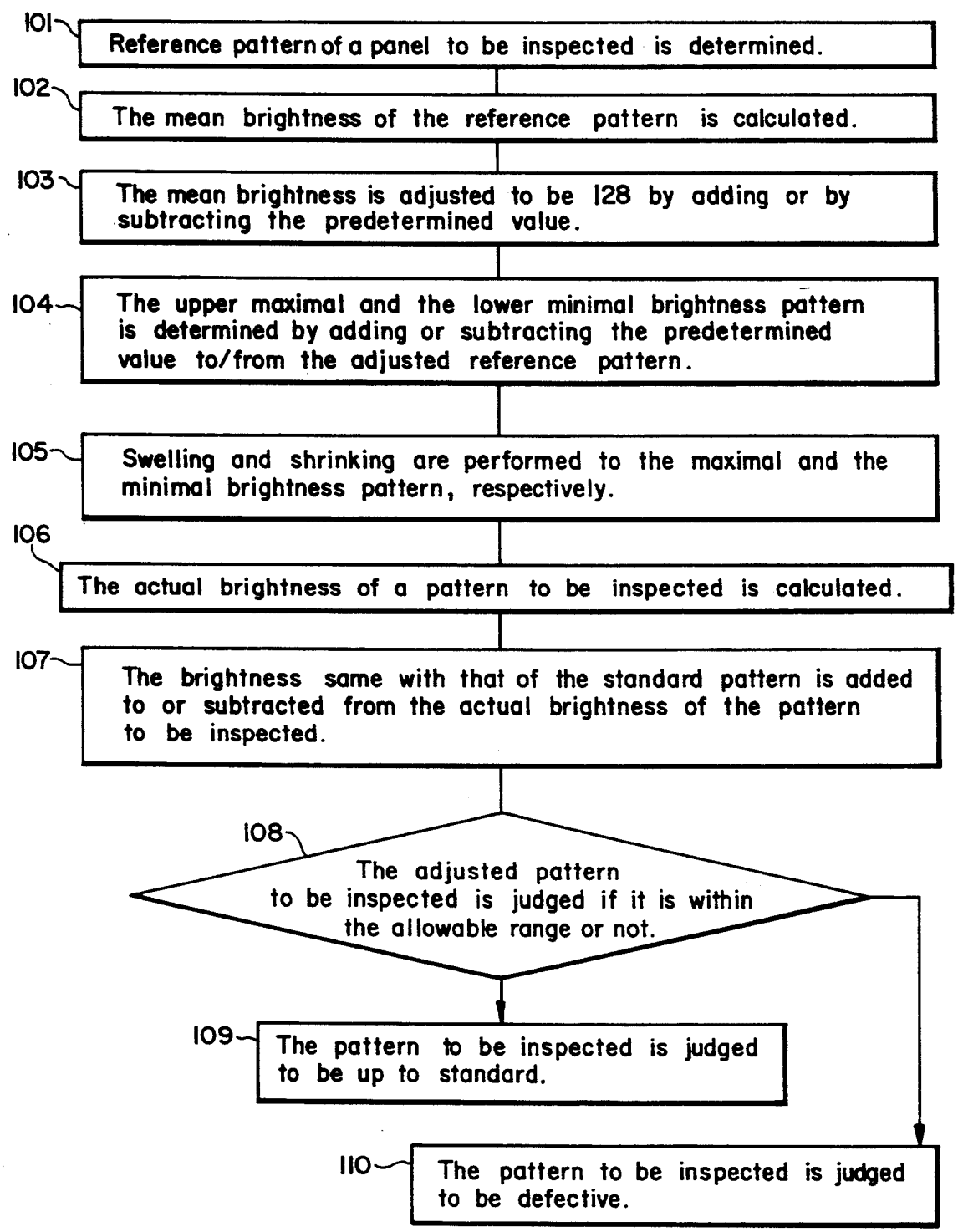
FIG. 1 shows a flowchart describing the method for determining if a liquid crystal panel to be inspected is defectless or not.

First, FIG. 1 is described here. It shows the process to determine if a liquid crystal panel is defective or not by comparing a pattern to be inspected with a reference pattern.

On step 101, the reference pattern of the panel to be inspected is determined. A liquid crystal panel can be divided into a single part which is a constituent, isolable, and an inspectable area. The "pattern" here means the single part as a unit area of image of the liquid crystal panel. Numerous cells constitute a liquid crystal panel. Here, a definite number of cells from within them are in the area. The reference pattern is determined by selecting a pattern which belongs to the group with the maximal number of similar characteristics among a plurality of patterns extracted at random.

On step 102, the reference pattern is inputted by a microscope and so forth and the mean brightness is calculated. On step 103, the mean brightness is adjusted to 128 by adding to or subtracting from the brightness of each pixel even if the actual mean brightness is, for example, 100 or 150, which makes it possible to inspect the brightness of a pattern to be inspected with the upper limit and the lower limit range. The value of 128 is the middle value of brightnesses shown with 256 levels.

Figure 2:
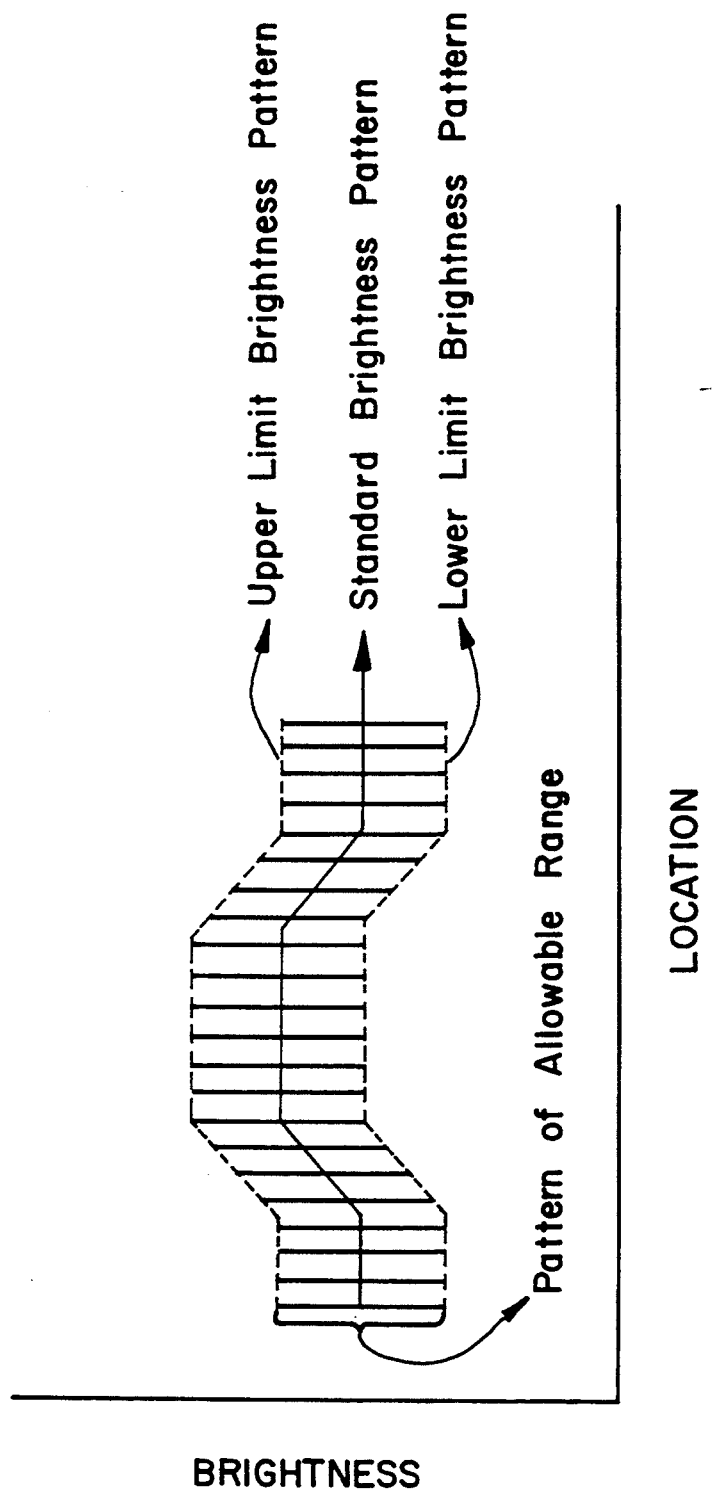
FIG. 2 shows a pattern with an allowable range.

On step 104, the predetermined value is added to or subtracted from the adjusted reference brightness pattern in order to determine the range of brightness. The patterns obtained by it is determined to be the upper limit brightness pattern and the lower limit brightness pattern, respectively, and a pattern between them is called the pattern within allowable range (FIG. 2). When the pattern to be inspected is within the allowable range, the liquid crystal panel to be inspected is judged to be up to standard, that is, to be defectless.

However, the accurate brightness of a pattern to be inspected cannot be calculated if the location of it is not exact and cannot reliably be inputted. In such a case, the pattern to be inspected can be judged to be defective even when it is within the allowable range, and vice versa, it can be judged to be up to standard when it is outside of the allowable range. In order to prevent this from happening, swelling is performed to the upper limit brightness pattern on step 105. Here, swelling is the processing to give the maximal brightness in a 3×3 convolution to the center pixel, which absorbs the difference of one pixel on, below, right-hand neighbor and left-hand neighbor the pixel of the pattern. In the same way, shrinking is performed to the pattern on the lower limit brightness. One shrinking on a 3×3 convolution can absorb the difference of one pixel in the same way as swelling. It is possible to avoid the error of calculation of brightness caused by the difference of the location on inputting a pattern to be inspected by performing such a processing.

On step 106 in inputting a pattern to be inspected by a microscope and so forth, the brightness of the pattern is calculated. On step 107, the same value as the reference pattern is added to or subtracted from each pixel of the pattern to be inspected.

On step 108, the pattern to be inspected which is adjusted on step 107 is to determine if it is within the allowable range or not. When it is within the allowable range, it is judged to be up to standard on step 109. On the other hand, when it exceeds the upper limit value or is below the lower limit value, the pattern to be inspected is judged to be defective.

As mentioned above, it is possible for unskilled individuals to inspect the total surface of a liquid crystal panel accurately and in a short time by the present invention.

What is claimed is:

1. A method for inspecting a liquid crystal panel, said liquid crystal panel being divided into a plurality of single parts which are each constituent, isolable, and inspectable, each of said single parts being a unit area of an image which is a pattern to be inspected to judge whether it is defective by comparing said pattern to be inspected with a reference pattern recorded beforehand, said method comprising the steps of:

selecting a unit area of an image without a defect from a liquid crystal panel to be inspected;

generating an upper limit reference pattern from a reference pattern by adding a predetermined upper limit brightness to each pixel of said reference pattern;

setting a brightness of each pixel in said upper limit brightness pattern equal to a maximum pixel brightness in a neighborhood of said pixel to obtain a processed upper limit brightness pattern;

generating a lower limit reference pattern from said reference pattern by subtracting a predetermined lower limit brightness to each pixel of said reference pattern;

setting a brightness of each pixel in said lower limit brightness pattern equal to a minimum pixel brightness in a neighborhood of said pixel to obtain a processed lower limit brightness pattern;

comparing a brightness of each pixel of the processed upper limit reference pattern with a brightness of a corresponding pixel of a pattern to be inspected;

comparing a brightness of each pixel of the processed lower limit reference pattern with a brightness of a corresponding pixel of a pattern to be inspected;

determining that the liquid crystal panel to be inspected is acceptable when more than a predetermined number of pixels have a brightness between brightnesses of corresponding pixels in said processed upper limit reference pattern and said processed lower limit reference pattern and that the liquid crystal panel to be inspected is not acceptable when less than said predetermined number of pixels have a brightness between the brightnesses of said corresponding pixels.

2. A method for inspecting a liquid crystal panel as claimed in claim 1, wherein said unit area of image comprises a predetermined number of cells.

3. A method for inspecting a liquid crystal panel as claimed in claim 1, further comprising a step of:
normalizing pixel brightnesses in said panel to be inspected so that a mean pixel brightness is 128.

4. A method for inspecting a liquid crystal panel as claimed in claim 1, said upper limit brightness pattern setting step comprising a step of:
swelling brightnesses of pixels in the upper limit reference pattern.

5. A method for inspecting a liquid crystal panel as claimed in claim 1, said lower limit brightness pattern setting step comprising a step of:
shrinking brightnesses of pixels in the lower limit reference pattern.

6. A method for inspecting a liquid crystal panel as claimed in claim 1, further comprising a step of:
selecting said reference pattern from a plurality of reference patterns, said reference pattern having a maximum number of similar characteristics with said pattern to be displayed.

7. A method for inspecting a liquid crystal panel as claimed in claim 1, said method further comprising the steps of:
normalizing pixel brightness in said reference pattern by adding or subtracting a constant value from each pixel in said reference pattern; and
adjusting pixel brightness in said pattern to be inspected by adding or subtracting said constant value from each pixel in said pattern to be inspected.

* * * * *